US008580307B2

(12) United States Patent
Jamiolkowski et al.

(10) Patent No.: US 8,580,307 B2
(45) Date of Patent: Nov. 12, 2013

(54) HIGH GLASS TRANSITION TEMPERATURE ABSORBABLE MICROSPHERES

(75) Inventors: Dennis D. Jamiolkowski, Long Valley, NJ (US); Modesto Erneta, Princeton Junction, NJ (US); Robert DiLuccio, Asbury, NJ (US)

(73) Assignee: Ethicon, Inc., Somverville, NJ (US)

( * ) Notice: Subject to any disclaimer, the term of this patent is extended or adjusted under 35 U.S.C. 154(b) by 1535 days.

(21) Appl. No.: 11/472,830

(22) Filed: Jun. 22, 2006

(65) Prior Publication Data
US 2007/0298114 A1   Dec. 27, 2007

(51) Int. Cl.
*A61K 9/14*   (2006.01)

(52) U.S. Cl.
USPC .......................................... 424/489; 514/951

(58) Field of Classification Search
USPC ................................................ 424/489, 501
See application file for complete search history.

(56) References Cited

U.S. PATENT DOCUMENTS

| | | | |
|---|---|---|---|
| 5,000,886 A | | 3/1991 | Lawter et al. |
| 5,236,355 A | | 8/1993 | Brizzolara et al. |
| 6,126,919 A | * | 10/2000 | Stefely et al. .................. 424/45 |
| 6,682,348 B2 | | 1/2004 | Lawter |
| 6,716,251 B1 | | 4/2004 | Asius et al. |
| 2006/0173060 A1 | * | 8/2006 | Chang et al. .................. 514/389 |

FOREIGN PATENT DOCUMENTS

| | | |
|---|---|---|
| EP | 0 711 548 A | 5/1996 |
| EP | 1 535 633 A | 6/2005 |
| WO | WO 2007073596 A1 * | 7/2007 |

OTHER PUBLICATIONS http://en.wikipedia.org/wiki/Microsphere, May 5, 2010.*
Encyclopedia of Pharmaceutical Technology, 2006, 3rd ed. pp. 2315.*
Laeschke Klaus, "Biocompatibility of Microparticles into Soft Tissue Fillers", Seminars in Cutaneous Medicine and Surgery, vol. 23, 2004, pp. 214-217, XP002457397.
Tipton, A.J. et al., "Synthetic Biodegradable Polymers as Medical Devices", Medical Plastics and Biomaterials (1998) 3.

* cited by examiner

*Primary Examiner* — James Rogers
(74) *Attorney, Agent, or Firm* — E. Richard Skula

(57) ABSTRACT

Absorbable microspheres comprising a copolymer formed from greater than 80 to about 99 mole percent D,L-lactide, L(−)-lactide, D(+)-lactide, or meso-lactide and combinations thereof, and about 1 to less than 20 mole percent of a different second monomer selected from the group consisting of p-dioxanone and trimethylene carbonate and combinations thereof, said microspheres having a particle size ranging from about 5 to 2000 microns. Also described herein are formulations comprising such absorbable microspheres.

15 Claims, No Drawings

HIGH GLASS TRANSITION TEMPERATURE ABSORBABLE MICROSPHERES

FIELD OF THE INVENTION

The present invention is directed to absorbable microspheres that may be used as fillers and formulations comprising such absorbable microspheres.

BACKGROUND

A filler is ideally easy to use and produces reproducible and long-lasting results. For example, it may be desirable for the filler to be comprised of microspheres that can pass through a small needle for injection subcutaneously or intradermally, without aggregrating or agglomerating under pressure, thereby avoiding clogging of a delivery device such as a needle. Further, if microspheres are utilized, it is desirable for the microspheres to retain their distinct spherical shape without aggregating or agglomerating (hereinafter referred to as "dimensional stability"), upon manufacture, storage and physical transport. Finally, in some situations, it may desirable for these microspheres to retain their distinct spherical shape after implantation, to avoid agglomeration of the microspheres subcutaneously or interdermally, which would produce an unnatural appearance in the skin.

U.S. Pat. No. 6,716,251 describes absorbable microspheres or microparticles suspended in a gel, where the microspheres or microparticles may be polycaprolactones, polylactides, polyglycolides and their copolymers.

Although this reference suggests the use of copolymers of polycaprolactones, polylactides, and polyglycolides, preferred polymers are poly-L-lactic acid, poly-D-lactic acid, or a mixture thereof, having a molecular mass ranging from between 70,000 and 175,000 Dalton, and preferably between 120,000 and 170,000 Dalton. It is believed that the polylactide microspheres exemplified in U.S. Pat. No. 6,716,251 would have sufficient crystallinity to be dimensionally stable since poly-L-lactides and poly-D-lactides are known to be highly crystalline.

It is possible to achieve the aforementioned property, i.e., dimensional stability, for example, by utilizing amorphous copolymers of D,L-lactide or meso-lactide to make microspheres having sufficient glass transition temperature to maintain their distinct spherical shape during manufacture, storage, transportation and use. Additionally, it is desirable to utilize copolymers of D,L-lactide or meso-lactide, of specific molecular weights to make microspheres that can be absorbed in the human body within 6 to 24 months after implantation.

More specifically, it is desirable to utilize absorbable amorphous copolymers of D,L-lactide or meso-lactide, having sufficient glass transition temperature, to make microspheres that may be used, for example, in plastic surgery applications and that retain their distinct spherical shape upon manufacture, storage, and physical transportation.

SUMMARY OF THE INVENTION

The present invention is directed to absorbable microspheres comprising an amorphous copolymer formed from greater than 80 to about 99 mole percent D,L-lactide or meso-lactide, and about 1 to less than 20 mole percent of a different second monomer selected from the group consisting of p-dioxanone or trimethylene carbonate and combinations thereof, said microspheres having a particle size ranging from about 5 to 2000 microns. Also described herein are formulations comprising such absorbable microspheres.

DETAILED DESCRIPTION

Described herein are amorphous copolymers of D,L-lactide or meso-lactide, and at least a different second monomer selected from the group consisting of p-dioxanone or trimethylene carbonate, that are absorbable within 6 to 24 months and that may be used to make microspheres having a particle size ranging from about 5 to 2000 microns, and preferably from about 30 to 75 microns. The microspheres described herein are capable of retaining their distinct spherical shape during manufacture, storage, and physical transportation.

The term "amorphous" as used herein refers to a morphological state having a crystallinity level less than 5%.

The amount of D,L-lactide or meso-lactide present in the copolymer described herein ranges from greater than 80 to about 99 mol %, and preferably from about 88 to 97%. The amount of the different second monomer ranges from about 1 to less than 20 mol %, and preferably from about 3 to 12 mol %.

Further, the copolymer is ideally a randomized copolymer, having a molecular weight ranging from about 1,000 to about 50,000 daltons, preferably from about 5,000 to 30,000 daltons, and most preferably from about 15,000 to 23,000 daltons. Ideally, the copolymer exhibits a single glass transition temperature greater than 40° C., as measured by differential scanning calorimetry (DSC).

The microspheres described herein may be made by coacervation, solvent evaporation, and droplet extrusion with a spinning disk. Other methods of manufacture that may be utilized for formation of microspheres include but are not limited to spray coating, pan-coating, spray-drying, phase separation, emulsion polymerization, and interfacial polymerization.

The microspheres described herein may be incorporated into a formulation that is suitable for delivery into the human body via, for example, a syringe. In particular, the formulation may comprise the microspheres suspended in a gel. As an example, the formulation may comprise the microspheres, water and a gelling agent approved for use in injections, such as cellulose derivatives, including but not limited to carboxymethylcellulose (CMC), at a concentration by mass ranging from about 0.1 to 7.5%, and preferably from about 0.1 to 5.0%, or hyaluronic acid at a concentration of up to 2% by weight when the formulation is to be used for intraocular injections and subcutaneous injections. Additional gelling agents include but are not limited to hydroxypropyl-methyl-cellulose (HPMC), which is commonly used in intraocular injection during cataract operations; lactic acid esters, caproic acid esters and the like.

Optionally, the formulation may comprise a surfactant, including but not limited to polyoxyethylene sorbitan monooleate (marketed under the brandname Tween 80), Span 20 or pluronic acid, in order to improve the homogeneity of the formulation or gel.

The formulation may be packaged in ready-for-use pre-filled sterile syringes, or in vials. Alternatively, the formulation may be packaged in a vial as freeze-dried product accompanied by a separate ampuole of sterile fluid (i.e., water for injection) that may be combined prior to use; or in a two-compartment pre-filled syringe, one containing the freeze-dried formulation, the other containing water, saline or intravenous solutions or other organic carriers.

It should be noted that the lactide used to make the microspheres of the present invention may be L(−)-lactide, D(+)- lactide, meso-lactide or combinations thereof. It is possible, however, to make microspheres having a small degree of crystallinity, greater than about 5%, when the lactide isomers L(−)-lactide or D(+)-lactide are in greater than 80 mole percent.

While the following examples demonstrate certain embodiments of the invention, they are not to be interpreted as limiting the scope of the invention, but rather as contributing to a complete description of the invention.

Example 1

Synthesis of a D,L-Lactide/PDO Copolymer at a 89:11(mol/mol) Composition. (89/11 D,L-Lactide/PDO)

Into a 500 ml round bottom flask provided with mechanical stirrer is charged 256.53 grams (1.78 moles) of D,L-lactide, 22.44 grams (0.22 moles) Paradioxanone (PDO), 1.52 grams (0.02 moles) of glycolic acid, and 0.242 ml. of a 0.33 molar solution of stannous octoate in toluene. The flask is put under vacuum for one hour. The flask is purged with nitrogen, and it is immersed in a hot oil bath kept at 160° C. for 16 hours, then at 120° C. for 2 hours and then at 110° C. for 2 hours. After cooling to room temperature, the flask is covered with foil and it is immersed in liquid nitrogen. The polymer is deglassed and it is ground and devolatilized under vacuum. The polymer is then extracted with excess octamethylcyclotetrasiloxane, after which it is dried extensively under vacuum at about 40° C.

The molar composition of the polymer by $^1$H NMR analysis is:

| | |
|---|---|
| PLA | 91.1% |
| PDS | 8.9% |
| lactide | 0.0% |
| PDO | 0.0% |

The weight average molecular weight is 15,400 Daltons. The glass transition temperature is 48° C.

Formation of Microspheres from the 89/11 D,L-Lactide/PDO Copolymer:

Microspheres are formed in a 2 liter resin flask provided with stirrer, nitrogen inlet, condenser and cold trap by the following solvent evaporation process. The flask is charged with 1,599 grams of a 3% w/w polyvinyl alcohol water solution. Stirrer rotation is set at about 241 RPM. A 7.5% w/w solution of the 89/11 D,L-lactide/PDO copolymer in methylene chloride (270 grams of solution) is added over a period of about 14 minutes into the side of the vortex, forming an oil in water emulsion. Methylene choride is evaporated by passing nitrogen over the surface of the solution for about 16 hours. The agitation is stopped and the formed microspheres are allowed to settle at the bottom of the flask and the supernatant liquid is removed. The microspheres are repeatedly washed with deionized water, allowing time for settling of the microspheres at the bottom of the flask before removing the supernatant liquid. The microspheres are wet-screened from the water slurry using two stacked stainless steel screens (screen sizes 38 microns and 75 microns) and collecting the fraction between 38 and 75 microns. The microspheres are then vacuum dried at room temperature until removal of water is accomplished. A total of 8.06 grams of microspheres is collected, giving a yield of 39.8%.

What is claimed:

1. Absorbable microspheres comprising an amorphous copolymer formed from greater than 80 to about 99 mole percent meso-lactide and about 1 to less than 20 mole percent of a different second monomer selected from the group consisting of p-dioxanone and trimethylene carbonate and combinations thereof, said microspheres having a diameter ranging from about 5 to about 90 microns, wherein said copolymer has a Tg greater than about 40° C. and a molecular weight of between about 15,000 to 23,000 Daltons, and wherein said microspheres have dimensional stability.

2. The absorbable microspheres of claim 1, wherein said copolymer is formed from about 88 to 97 mole percent meso-lactide and about 3 to 20 mole percent of the different second monomer.

3. The absorbable microspheres of claim 2, wherein said copolymer has a Tg greater than 50° C.

4. The absorbable microspheres of claim 2, said copolymer having a molecular weight of between 6,000 to about 30,000 Daltons.

5. The absorbable microspheres of claim 1, wherein said second monomer is p-dioxanone.

6. The absorbable microspheres of claim 2, wherein said microspheres are absorbed at physiological conditions in less than 24 months.

7. A formulation comprising:
(a) absorbable microspheres comprising an amorphous copolymer formed from greater than 80 to about 99 mole percent meso-lactide and about 1 to less than 20 mole percent of a different second monomer selected from the group consisting of p-dioxanone and trimethylene carbonate and combinations thereof, said microspheres having a diameter ranging from about 5 to about 90 microns, wherein said copolymer has Tg greater than about 40° C. and a molecular weight of between about 15,000 to 23,000 Daltons, and wherein said microspheres have dimensional stability; and
(b) from about 0.1 to 7.5% (wt/wt) of a gelling agent.

8. The formulation of claim 7, further comprising a fluid selected from the group consisting of water, saline, intravenous solution, and organic carriers.

9. The formulation of claim 7, wherein said gelling agent is a cellulose derivative.

10. The formulation of claim 9, wherein said cellulose derivative is at least one member selected from the group consisting of carboxymethylcellulose and hydroxypropylmethylcellulose.

11. The formulation of claim 7, wherein said gelling agent is hyaluronic acid.

12. The formulation of claim 7, further comprising at least one surfactant selected from the group consisting of polyoxyethylene sorbitan monooleate and polyoxyethylene-polyoxypropylene block copolymer surfactant.

13. Absorbable microspheres comprising an amorphous copolymer formed from greater than 80 to about 99 mole percent meso-lactide, and about 1 to less than 20 mole percent of a different second monomer selected from the group consisting of p-dioxanone and trimethylene carbonate and combinations thereof, said microspheres having a diameter ranging from about 5 to 2000 microns, wherein said copolymer has a Tg greater than about 40° C. and a molecular weight of between about 15,000 to 23,000 Daltons, and wherein said microspheres have dimensional stability.

14. The absorbable microspheres of claim 13, wherein said copolymer is formed from about 88 to 97 mole percent meso-lactide and about 3 to 20 mole percent of p-dioxanone.

15. A formulation comprising:
(a) absorbable microspheres comprising an amorphous copolymer formed from greater than 80 to about 99 mole lactide selected from the group consisting of meso-lactide and about 1 to less than 20 mole percent of a different second monomer selected from the group consisting of p-dioxanone and trimethylene carbonate and combinations thereof, said microspheres having a diameter ranging from about 5 to about 90 microns, wherein said copolymer has a Tg greater than about 40° C. and a molecular weight of between about 15,000 to 23,000 Daltons, and wherein said microspheres have dimensional stability; and
(b) from about 0.1 to 7.5% (wt/wt) of a gelling agent.

* * * * *